United States Patent
Sweeney et al.

(10) Patent No.: US 10,143,385 B2
(45) Date of Patent: *Dec. 4, 2018

(54) METHODS AND APPARATUS FOR STRATIFYING RISK OF HEART FAILURE DECOMPENSATION

(71) Applicant: Cardiac Pacemakers, Inc., St. Paul, MN (US)

(72) Inventors: Robert J. Sweeney, Woodbury, MN (US); Yi Zhang, Plymouth, MN (US); Qi An, Blaine, MN (US); Pramodsingh Hirasingh Thakur, Woodbury, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 1145 days.

This patent is subject to a terminal disclaimer.

(21) Appl. No.: 14/282,353

(22) Filed: May 20, 2014

(65) Prior Publication Data

US 2014/0343439 A1 Nov. 20, 2014

Related U.S. Application Data

(60) Provisional application No. 61/825,181, filed on May 20, 2013.

(51) Int. Cl.
*A61B 5/02* (2006.01)
*A61B 5/0205* (2006.01)
(Continued)

(52) U.S. Cl.
CPC ............ *A61B 5/0205* (2013.01); *A61B 5/024* (2013.01); *A61B 5/02028* (2013.01);
(Continued)

(58) Field of Classification Search
CPC ... A61B 5/0205; A61B 5/7275; A61B 5/7282; A61B 5/0245; A61B 5/024;
(Continued)

(56) References Cited

U.S. PATENT DOCUMENTS

| | | |
|---|---|---|
| 917,078 A | 4/1909 | Kroedel |
| 2,008,581 A | 7/1935 | Dennison et al. |

(Continued)

FOREIGN PATENT DOCUMENTS

| | | |
|---|---|---|
| AU | 2009293198 | 10/2013 |
| CN | 101765400 A | 6/2010 |

(Continued)

OTHER PUBLICATIONS

"U.S. Appl. No. 12/561,721, Non Final Office Action dated Feb. 29, 2012", 8 pgs.

(Continued)

*Primary Examiner* — Navin Natnithithadha
*Assistant Examiner* — Andrey Shostak
(74) *Attorney, Agent, or Firm* — Schwegman Lundberg & Woessner, P.A.

(57) ABSTRACT

Devices and methods for identifying patient at elevated risk of developing future heart failure (HF) events, such as events indicative of HF decompensation status, are described. The devices and methods can stratify the risk using sensor signals or signal metrics selected in accordance with patient chronic conditions. A medical device can receive a patient status input including at least a first and a second chronic condition indicators, sense one or more physiologic signals from the patient, and generate a plurality of signal metrics from the physiologic signals when the first chronic condition indicator and the second chronic condition indicator meets respective criterion. One or more patient-specific signal metrics can be selected from a group includ- (Continued)

ing the signal metrics selected for both the first and the second chronic conditions. A risk stratification algorithm can use the selected one or more patient-specific signal metrics to compute a composite risk index indicative of the probability of the patient later developing an event indicative of worsening of HF.

20 Claims, 6 Drawing Sheets

(51) Int. Cl.

| | | |
|---|---|---|
| A61B 5/08 | (2006.01) | |
| A61B 5/145 | (2006.01) | |
| A61B 5/00 | (2006.01) | |
| A61B 5/20 | (2006.01) | |
| A61B 5/024 | (2006.01) | |
| A61B 5/0245 | (2006.01) | |
| G06F 19/00 | (2018.01) | |

(52) U.S. Cl.
CPC ............. *A61B 5/0245* (2013.01); *A61B 5/08* (2013.01); *A61B 5/0826* (2013.01); *A61B 5/14532* (2013.01); *A61B 5/201* (2013.01); *A61B 5/4818* (2013.01); *A61B 5/7275* (2013.01); *A61B 5/7282* (2013.01); *G06F 19/00* (2013.01); *A61B 5/0031* (2013.01)

(58) Field of Classification Search
CPC ... A61B 5/02028; A61B 5/08; A61B 5/14532; A61B 5/0826; A61B 5/4818; A61B 5/201; A61B 5/0031
See application file for complete search history.

(56) References Cited

U.S. PATENT DOCUMENTS

| | | | |
|---|---|---|---|
| 6,080,106 | A | 6/2000 | Lloyd et al. |
| 6,454,705 | B1 | 9/2002 | Cosentino et al. |
| 6,556,977 | B1 | 4/2003 | Lapointe et al. |
| 6,678,669 | B2 | 1/2004 | Lapointe et al. |
| 6,821,249 | B2 | 11/2004 | Casscells, III et al. |
| 6,980,851 | B2 | 12/2005 | Zhu et al. |
| 7,127,290 | B2 | 10/2006 | Girouard et al. |
| 7,761,158 | B2 | 7/2010 | Brockway et al. |
| 8,223,023 | B2 | 7/2012 | Sachanandani et al. |
| 8,249,709 | B2 | 8/2012 | Davenport et al. |
| 8,346,360 | B2 | 1/2013 | Libbus et al. |
| 8,369,937 | B2 | 2/2013 | Bardy |
| 8,469,898 | B2 | 6/2013 | Zhang et al. |
| 9,351,647 | B2 | 5/2016 | Zhang et al. |
| 2003/0055461 | A1 | 3/2003 | Girouard et al. |
| 2003/0083556 | A1 | 5/2003 | Cosentino et al. |
| 2003/0092975 | A1 | 5/2003 | Casscells, III et al. |
| 2004/0034286 | A1 | 2/2004 | Kasper et al. |
| 2004/0122297 | A1 | 6/2004 | Stahmann et al. |
| 2004/0147982 | A1 | 7/2004 | Bardy |
| 2005/0080348 | A1 | 4/2005 | Stahmann et al. |
| 2005/0137481 | A1 | 6/2005 | Sheard et al. |
| 2005/0256550 | A1 | 11/2005 | Gilkerson et al. |
| 2006/0010090 | A1 | 1/2006 | Brockway et al. |
| 2006/0064030 | A1 | 3/2006 | Cosentino et al. |
| 2006/0116557 | A1 | 6/2006 | Moore et al. |
| 2006/0241712 | A1 | 10/2006 | Cates et al. |
| 2008/0126124 | A1 | 5/2008 | Schechter |
| 2008/0157980 | A1* | 7/2008 | Sachanandani ...... A61B 5/0031 340/573.1 |
| 2008/0162182 | A1* | 7/2008 | Cazares ................ G06Q 50/22 705/2 |
| 2010/0076321 | A1* | 3/2010 | Zhang .................. A61B 5/0205 600/483 |
| 2010/0094102 | A1 | 4/2010 | Zhang et al. |
| 2011/0009753 | A1* | 1/2011 | Zhang .................. A61B 5/0205 600/484 |
| 2011/0275942 | A1 | 11/2011 | Stahmann et al. |
| 2012/0157797 | A1 | 6/2012 | Zhang et al. |
| 2012/0157856 | A1 | 6/2012 | An et al. |
| 2012/0253207 | A1 | 10/2012 | Sarkar et al. |
| 2013/0197378 | A1* | 8/2013 | Dumont ............... A61B 5/7221 600/509 |
| 2013/0226011 | A1 | 8/2013 | Zhang et al. |
| 2014/0343438 | A1 | 11/2014 | Sweeney et al. |
| 2016/0228072 | A1 | 8/2016 | Zhang et al. |

FOREIGN PATENT DOCUMENTS

| | | |
|---|---|---|
| CN | 102176861 A | 9/2011 |
| CN | 102355852 A | 2/2012 |
| CN | 105246397 A | 1/2016 |
| EP | 0917078 A1 | 5/1999 |
| EP | 2008581 B1 | 8/2011 |
| JP | 2006510447 A | 3/2006 |
| JP | 2006510451 A | 3/2006 |
| JP | 2007053436 A | 3/2007 |
| JP | 2007534363 A | 11/2007 |
| JP | 2008053660 A | 3/2008 |
| JP | 2008536607 A | 9/2008 |
| JP | 2009518731 A | 5/2009 |
| JP | 2010514497 A | 5/2010 |
| JP | 2010514498 A | 5/2010 |
| JP | 2012502752 | 2/2012 |
| JP | 2016523600 A | 8/2016 |
| WO | WO-2008121185 A1 | 10/2008 |
| WO | WO-2010033699 A1 | 3/2010 |
| WO | WO-2014189885 A1 | 11/2014 |

OTHER PUBLICATIONS

"U.S. Appl. No. 12/561,721, Non Final Office Action dated Oct. 16, 2012", 7 pgs.
"U.S. Appl. No. 12/561,721, Non-Final Office Actions dated Apr. 29, 2011", 6 pgs.
"U.S. Appl. No. 12/561,721, Notice of Allowance dated Feb. 22, 2013", 5 pgs.
"U.S. Appl. No. 12/561,721, Response filed Jan. 16, 2013 to Non Final Office Action dated Oct. 16, 2012", 9 pgs.
"U.S. Appl. No. 12/561,721, Response filed May 22, 2012 to Non Final Office Action dated Feb. 29, 2012", 9 pgs.
"U.S. Appl. No. 12/561,721, Response filed Aug. 29, 2011 to Non-Final Office Action dated Apr. 29, 2011", 13 pgs.
"U.S. Appl. No. 13/858,631, Preliminary Amendment filed Apr. 9, 2013", 8 pgs.
"Australian Application Serial No. 2009293198, Office Action dated May 7, 2012", 3 pgs.
"Australian Application Serial No. 2009293198, Subsequent Examiners Report dated Dec. 7, 2012", 8 pgs.
"European Application Serial No. 09792660.4, Office Action Response filed Dec. 22, 2011", 14 pgs.
"International Application Serial No. PCT/US2009/057316 International Preliminary Report on Patentability dated Mar. 31, 2011", 7 pgs.
"International Application Serial No. PCT/US2009/057316, International Search Report dated Dec. 23, 2009", 5 pgs.
"International Application Serial No. PCT/US2009/057316, Written Opinion dated Dec. 23, 2009", 8 pgs.
"Japanese Application Serial No. 2009293198, Response filed Apr. 2, 2013 to Non Final Office Action dated Nov. 22, 2012", 16.
"Japanese Application Serial No. 2009293198, Response filed Oct. 8, 2012 to Non Final Office Action dated May 7, 2012", 18.
"Japanese Application Serial No. 2011-527959, Office Action dated Feb. 19, 2013", (w/ English Translation), 6 pgs.
Anand, I. S, et al., "Design and Performance of a Multisensor Heart Failure Monitoring Algorithm: Results From the Multisensor Monitoring in Congestive Heart Failure (MUSIC) Study", Journal of Cardiac Failure, 18(4), (Apr. 2012), 289-295.

(56) References Cited

OTHER PUBLICATIONS

Ekman, I., et al., "Exploring Symptoms in Chronic Heart Failure", The European Journal of Heart Failure, 7, (2005), 699-703.
Ingle, L., et al., "Perception of Symptoms is Out of Proportion to Cardiac Pathology in Patients With "Diastolic Heart Failure"", Heart, 94, (2008), 748-753.
Lavietes, M., et al., "Dyspnea and Symptom Amplification in Asthma", Respiration, 75(2), (2008), 158-162.
Skotzko, C. E., "Symptom Perception in CHF: (why mind matters)", Heart Failure Reviews, [Epub Dec. 11, 2007], (prior to Jun. 13, 2008), 6 pages.
"U.S. Appl. No. 13/858,631, Final Office Action dated Oct. 22, 2015", 6 pgs.
"U.S. Appl. No. 13/858,631, Non Final Office Action dated May 29, 2015", 10 pgs.
"U.S. Appl. No. 13/858,631, Notice of Allowance dated Feb. 4, 2016", 5 pgs.
"U.S. Appl. No. 13/858,631, Response filed Aug. 31, 2015 to Non Final Office Action dated May 29, 2015", 14 pgs.
"U.S. Appl. No. 13/858,631, Response filed Dec. 14, 2015 to Final Office Action dated Oct. 22, 2015", 8 pgs.
"U.S. Appl. No. 14/282,283, Final Office Action dated Aug. 1, 2017", 12 pgs.
"U.S. Appl. No. 14/282,283, Non Final Office Action dated Jan. 30, 2017", 13 pgs.
"U.S. Appl. No. 14/282,283, Response filed Apr. 13, 2017 to Non Final Office Action dated Jan. 30, 2017", 12 pgs.
"U.S. Appl. No. 15/132,738, Preliminary Amendment filed Apr. 26, 2016", 6 pgs.
"Application Serial No. PCT/US2014/038720, International Preliminary Report on Patentability dated Dec. 3, 2015", 6 pgs.
"Chinese Application Serial No. 201480029099.6, Office Action dated Mar. 14, 2017", w/ English translation, 18 pgs.
"Chinese Application Serial No. 201480029099.6, Response filed Jul. 28, 2017 to Office Action dated Mar. 14, 2017", w/ claims in English, 15 pgs.
"International Application Serial No. PCT/US2014/038720, International Search Report dated Jul. 21, 2014".
"International Application Serial No. PCT/US2014/038720, Written Opinion dated Jul. 21, 2014".
"Japanese Application No. 2016-514999, Response filed Feb. 1, 2017 to Office Action dated Nov. 1, 2016", w/ Claims in English, 12 pgs.
Boehmer, John P., et al., "A Multisensor Algorithm Predicts Heart Failure Events in Patients With Implanted Devices", JACC: Heart Failure, vol. 5, No. 3, 2017, pp. 216-225.

\* cited by examiner

METHODS AND APPARATUS FOR STRATIFYING RISK OF HEART FAILURE DECOMPENSATION

CLAIM OF PRIORITY

This application claims the benefit of priority under 35 U.S.C. § 119(e) of U.S. Provisional Patent Application Ser. No. 61/825,181, filed on May 20, 2013, which is herein incorporated by reference in its entirety decompensation.

TECHNICAL FIELD

This document relates generally to medical devices, and more particularly, to systems, devices and methods for detecting and monitoring heart failure decompensation.

BACKGROUND

Congestive heart failure (CHF) is a major health problem and affects over five million people in the United States alone. CHF patients typically have enlarged heart with weakened cardiac muscles, resulting in poor cardiac output of blood. Elevated pulmonary vascular pressures can cause fluid accumulation in the lungs over time. In many CHF patients, fluid accumulation precedes episodes of heart failure (HF) decompensation. The HF decompensation can be characterized by pulmonary or peripheral edema, reduced cardiac output, and symptoms such as fatigue, shortness of breath and the like.

Overview

Frequent monitoring of CHF patients and timely detection of intrathoracic fluid accumulation or other events indicative of HF decompensation status can help prevent worsening of HF in CHF patients, hence reducing cost associated with HF hospitalization.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. The ambulatory or implantable medical devices can include physiologic sensors which can be configured to sense electrical activity and mechanical function of the heart, and the medical device can optionally deliver therapy such as electrical stimulation pulses to a target area, such as to restore or improve the cardiac function. Some of these devices can provide diagnostic features, such as using transthoracic impedance or other sensor signals. For example, fluid accumulation in the lungs decreases the transthoracic impedance due to the lower resistivity of the fluid than air in the lungs. The fluid accumulation can also elevate ventricular filling pressure, resulting in a louder S3 heart sound. Additionally, fluid accumulation in the lungs can irritate the pulmonary system and leads to decrease in tidal volume and increase in respiratory rate.

Identification of patient at an elevated risk of developing future HF events such as worsening of HF can help ensure timely treatment, thereby improving the prognosis and patient outcome. On the other hand, identifying and safely managing the patients at low risk of future HF events can avoid unnecessary medical intervention and reduce healthcare cost. Desirable performance of a risk stratification method such as for assessing the risk of future HF events can include one or more of a high sensitivity, a high specificity, a high positive predictive value (PPV), or a negative predictive value (NPV). In the context of risk stratification for HF decompensation event, for example, the sensitivity can represent the accuracy of identifying high-risk patients (e.g., those more likely to develop a future HF decompensation episode). The specificity can represent the accuracy of identifying low-risk patients (e.g., those less likely to develop a future HF decompensation episode). Risk stratification have traditionally focused on the use of patient demographic data such as age, gender, or race; or predisposing risk factors such as hypertension, coronary artery disease, or prior HF hospitalization. However, factors such as difference of medical conditions across patients and/or disease progression within a patient can negatively affect the performance of risk stratification that relies on the traditional risk stratifiers. The present inventors have recognized that there remains a considerable need of systems and methods that can accurately identify CHF patients with elevated risk of developing future events of worsening of HF, such as future HF decompensation events.

Various embodiments described herein can help improve the process of identifying patient at elevated risk of developing future HF events such as events indicative of HF decompensation status. For example, a medical device (such as an implantable medical device or a wearable medical device) can stratify a patient's risk of developing a future HF event using sensors signals or signal metrics selected based on chronic conditions of the patient. A signal analyzer circuit can receive a patient status input which can include at least a first and a second chronic condition indicator. The second chronic condition indicator can be non-identical to the first chronic condition. The signal analyzer can sense one or more physiologic signals from the patient, and generate a plurality of signal metrics from the one or more physiologic signals. The signal metrics including a first set of one or more signal metrics when the first chronic condition indicator meets at least one first specified criterion, and a second set of signal metrics when the second chronic condition indicator meets at least one second specified criterion. The signal analyzer circuit can include a patient-specific signal metric selector circuit configured to select from the plurality of signal metrics one or more patient-specific signal metrics selected from a group including both the first set of one or more signal metrics and the second set of one or more signal metrics. The medical device can include a stratification circuit configured to generate a composite risk index using the selected one or more patient-specific signal metrics, where the composite risk index can be indicative of the probability of the patient later developing an event indicative of worsening of HF.

A method can include receiving at least a first chronic condition indicator and a second chronic condition indicator of a patient non-identical to the first chronic condition indicator, sensing one or more physiologic signals of the patient, and generating a plurality of signal metrics from the one or more physiologic signals. The signal metrics can include a first set of one or more signal metrics when the first chronic condition indicator meets at least one first specified criterion, and a second set of signal metrics when the second chronic condition indicator meets at least one second specified criterion. The method can include selecting from the plurality of signal metrics one or more patient-specific signal metrics selected from a group including both the first set of one or more signal metrics and the second set of one or more signal metrics, and generating a composite risk index using the selected one or more patient-specific signal metrics. The generated composite risk index can be indicative of the probability of the patient later developing an event indicative of worsening of HF.

This Overview is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for identifying patients with elevated risk of developing future events related to worsening of HF, such as an HF decompensation event. The risk stratification can be performed using the physiologic signals such as sensed from a physiologic sensor associated with a medical device such as an implantable pacemaker or defibrillator. The present inventors have recognized that patient chronic conditions, including patient demographic characteristics or patient chronic disease indicators, can affect certain types of sensor signals in HF patients. Therefore, by selecting sensor signals according to the patient chronic conditions and analyzing the signal metrics derived from the sensor signals, the present document can provide a method and device to predict the risk of future HF event such as worsening of HF, thereby allowing immediate medical attention to the patient.

Figure 1:
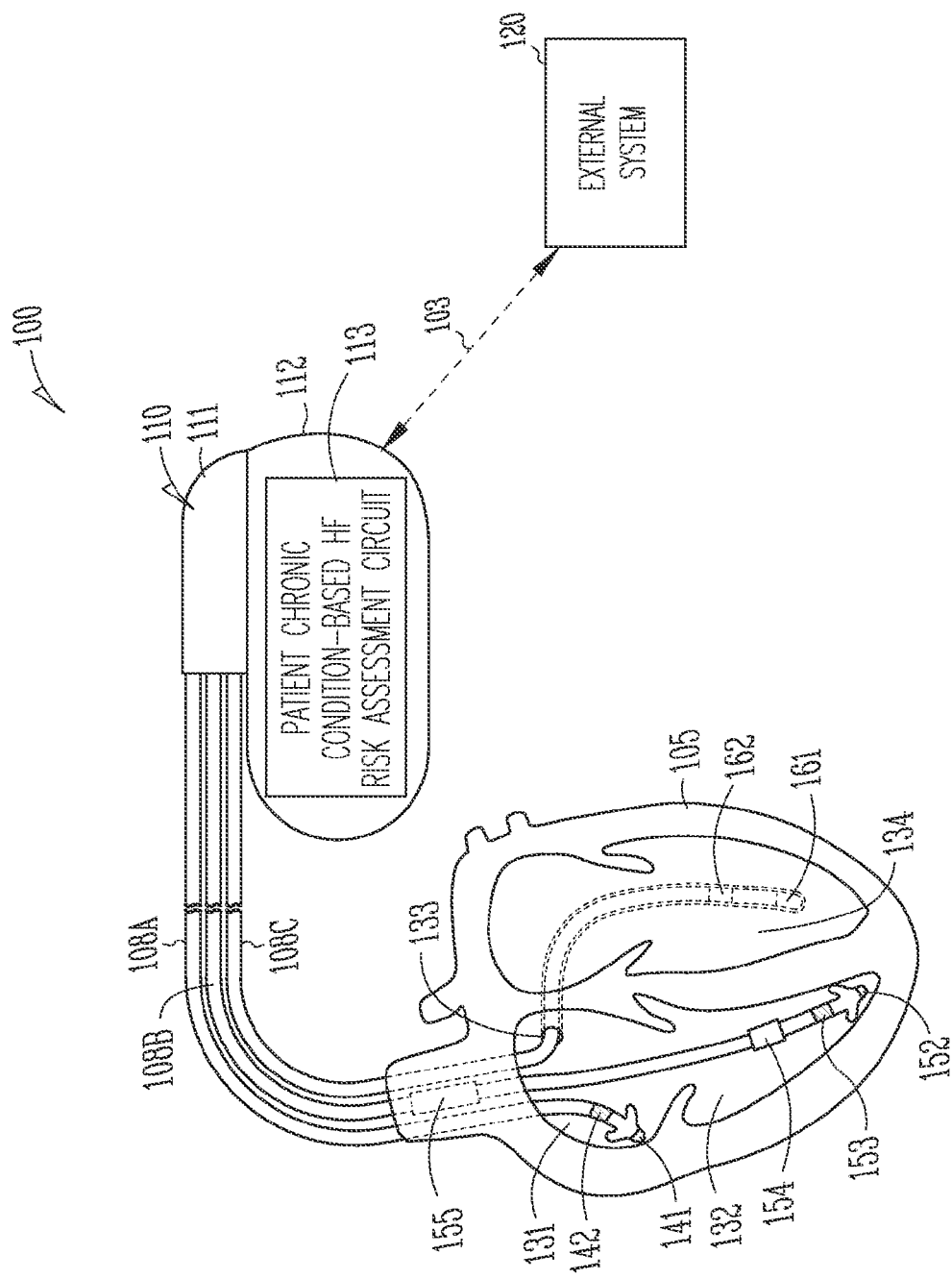
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiological signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The electrodes 161 and 162 can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiological signal. The physiological signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiological sensors that can be integrated within the IMD 110. The IMD 110 can also be configured to sense a physiological signal from one or more external physiologic sensors or one or more external electrodes that can be coupled to the IMD 110. Examples of the physiological signal can include one or more of heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are.

As illustrated, the CRM system 100 can include a patient chronic condition-based HF risk assessment circuit 113. The patient chronic condition-based HF risk assessment circuit 113 can include a signal analyzer circuit and a risk stratification circuit. The signal analyzer circuit can receive patient chronic condition indicators and one or more physiologic signals from the patient, and select one or more patient-specific sensor signals or signal metrics from the physiologic signals. The signal analyzer circuit can receive the physiologic signals from the patient using the electrodes on one or more of the leads 108A-C, or physiologic sensors deployed on or within the patient and communicated with the IMD 110. The risk stratification circuit can generate a composite risk index indicative of the probability of the patient later developing an event of worsening of HF (e.g., an HF decompensation event) such as using the selected patient-specific sensor signals or signal metrics. The HF decompensation event can include one or more early precursors of an HF decompensation episode, or an event indicative of HF progression such as recovery or worsening of HF status. Examples of patient chronic condition-based HF risk assessment circuit 113 are described below, such as with reference to FIGS. 2-3.

The external system 120 can allow for programming of the IMD 110 and can receives information about one or more signals acquired by IMD 110, such as can be received via a communication link 103. The external system 120 can include a local external IMD programmer. The external system 120 can include a remote patient management system that can monitor patient status or adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiological data acquired by the IMD 110, physiological data acquired by and stored in the IMD 110, therapy history data or data indicating IMD operational status stored in the IMD 110, one or more programming instructions to the IMD 110 such as to configure the IMD 110 to perform one or more actions that can include physiological data acquisition such as using programmably specifiable sensing electrodes and configuration, device self-diagnostic test, or delivery of one or more therapies.

The patient chronic condition-based HF risk assessment circuit 113 may be implemented at the external system 120, which can be configured to perform HF risk stratification such as using data extracted from the IMD 110 or data stored in a memory within the external system 120. Portions of patient chronic condition-based HF risk assessment circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
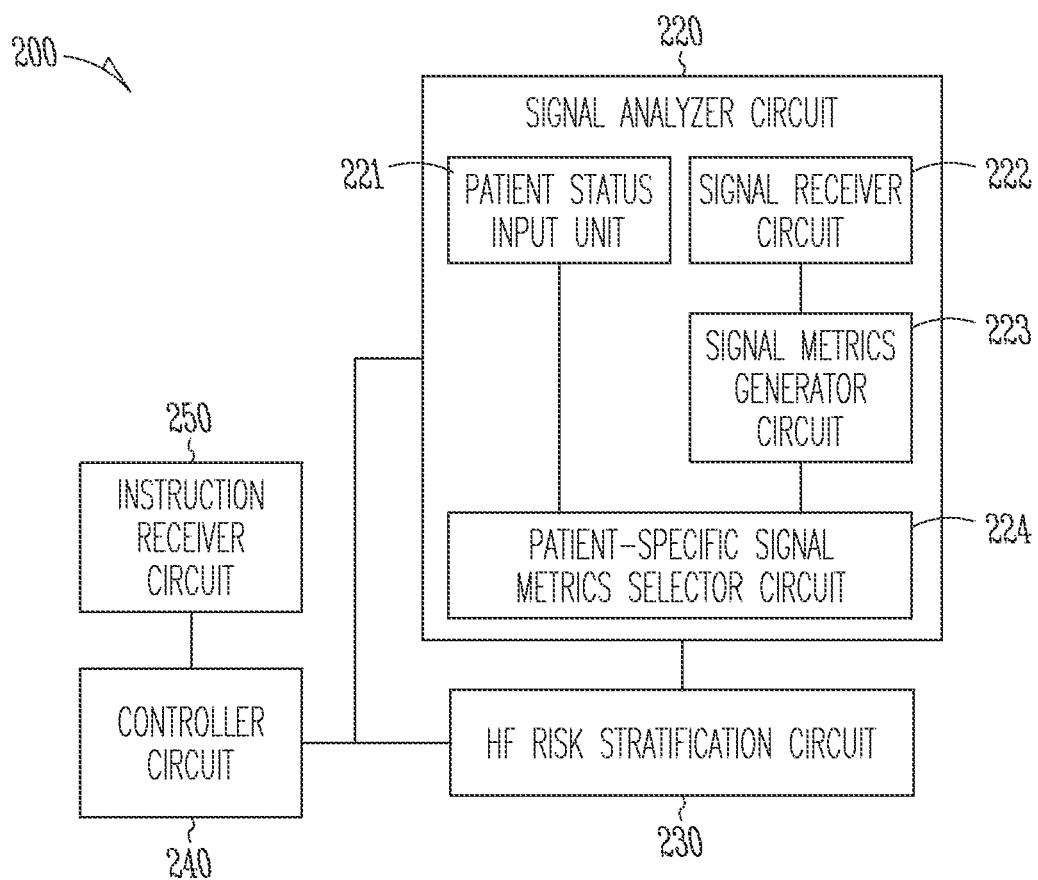
FIG. 2 illustrates an example of a patient chronic condition-based HF risk assessment circuit.

FIG. 2 illustrates an example of a patient chronic condition-based HF risk assessment circuit 200, which can be an embodiment of the patient chronic condition-based HF risk assessment circuit 113. The patient chronic condition-based HF risk assessment circuit 200 can include one or more of a signal analyzer circuit 220, an HF risk stratification circuit 230, a controller circuit 240, and an instruction receiver circuit 250.

The signal analyzer circuit 220 can include a patient status input unit 221, a signal receiver circuit 222, a signal metrics generator circuit 223, and a patient-specific signal metrics selector circuit 224. The patient status input unit 221 can be configured to receive at least a first chronic condition indicator and a second chronic condition indicator of a patient. The second chronic condition indicator can be non-identical to the first chronic condition indicator. The patient chronic condition indicators can be descriptive of the patient characteristics or sustained medical status that do not change or slowly change over a certain specified time, such as approximately at least six months. The first and the second chronic condition indicators of the patient can respectively include at least one of a chronic disease indicator of the patient, a prior medical procedure indicator of the patient, or a demographic characteristic indicator of the patient. Example of the chronic disease indicator of the patient can include a patient's prior myocardial infarction (MI), ischemic or dilated cardiomyopathy, valvular disease, renal disease, chronic obstructive pulmonary disease (COPD), peripheral vascular disease, cerebrovascular disease, hypertension, hepatic disease, diabetes, asthma, anemia, depression, pulmonary hypertension, sleep disordered breathing, hyperlipidemia, among others. Examples of the prior medical procedure can include prior coronary artery bypass graft (CABG) surgery, thoracic surgery, valvular surgery, or other surgical interventions. Example of demographic characteristic indicator can include a patient's age, sex, race, height, ethnicity, blood type, past or current smoker, New York heart association (NYHA) functional class, among others.

The patient status input unit 221 can be configured to receive at least the first and the second chronic condition indictors from a system user such as via the instruction receiver 250. In an example, the patient status input unit 221 can be configured to be coupled to a storage device, including an electronic medical record (EMR) system, that can store at least the first and the second chronic condition indicators of the patient. When receiving a command such as issued by a system user (e.g., a physician) such as via instruction receiver 250, the patient status input unit 221 can retrieve from the storage device such as the EMR system at least the first patient chronic status and the second patient chronic status. The first and the second chronic condition indicators can be non-identical. For example, the first chronic condition indictor includes an indicator of the patient's prior thoracic surgery, and the second chronic condition indicator includes an indicator of patient's having a renal disease.

The chronic condition indicators received by the patient status input unit 221 can include binary values indicating the presence or absence of a specified condition. Additionally or alternatively, the chronic condition indicators can include categorical classifications or progressive stages of a demographic characteristic indicator or a chronic disease indicator, such as stages of HF (e.g., NYHA classes I, II, III, and IV), diabetes mellitus type 1 and type 2, chronic kidney disease (CKD) of stage 1 through stage 5, among others. The chronic condition indicator can also include a plurality of value ranges of a physiologic parameter that indicate functional assessment of the patient's chronic condition. For example, the chronic condition indicators can include a plurality of value ranges of glomerular filtration rate (GFR) indicating the progression of CKD, a plurality of value ranges of ejection fraction (EF) indicating the progression of HF, a plurality of value ranges of blood glucose indicating the progression of diabetes, a plurality of value ranges of apnea hypopnea index (AHI) indicating the progression of sleep disordered breathing, a plurality of value ranges of forced expiratory volume in one second (FEV1) indicating the progression of chronic obstructive pulmonary diseases (COPD). The first and the second chronic condition indicators can respectively include non-identical categorical classes from the same or different chronic condition indicators of the patient.

The signal receiver circuit 222 can be configured to receive one or more physiologic signals from the patient. The signal receiver circuit 222 can be coupled to one or more of: one or more electrodes such as electrodes on one or more of the leads 108A-C or the can 112, one or more physiologic sensors, or one or more patient monitors. The signal receiver circuit 222 can be configured to sense a physiological signal that can be indicative of worsening of HF status. Examples of such a physiological signal can include one or more electrograms, such as from electrodes on one or more of the leads 108A-C or the can 112, heart rate, heart rate variability, intrathoracic impedance, intracardiac impedance, arterial pressure, pulmonary artery pressure, RV pressure, LV coronary pressure, coronary blood temperature, blood oxygen saturation, one or more heart sounds, physiologic response to activity, apnea hypopnea index, one or more respiration signals such as a respiration rate signal or a tidal volume signal. The signal receiver circuit 222 can include one or more modules to perform signal conditioning (e.g., signal amplification, digitization, or filtering) or parameter extraction from the sensed physiological signal. Examples of extracted signal parameters can include: signal mean, median, or other central tendency measures; a histogram of the signal intensity; one or more signal trends over time; one or more signal morphological descriptors; or signal power spectral density at a specified frequency range. In an example, the signal sensing circuit can sense two or more physiological signals and can generate a composite signal parameter set such as using the two or more physiological signals.

The signal metrics generator circuit 223 can be configured to generate a plurality of signal metrics from the one or more physiologic signals. A signal metric can include a sensor signal such as an analog or digitized time series acquired from a physiologic sensor or from one or more electrodes on one or more of the leads 108A-C or the can 112. A signal metric can also include a signal feature extracted from the sensor signal such as a statistical measure (e.g., mean, median, standard deviation, variance, correlation, covariance, or other statistical value over a specified time segment), a morphological measure (e.g., peak, trough, slope, area under the curve), or a feature indicative of a physiologic activity (e.g., P wave and QRS complexes in an electrogram signal, or S1, S2, S3 or S4 components of a heart sound signal, an inspiration phase and expiration phase of a respiration signal). The signal metrics generated by the signal metrics generator circuit 223 can include at least a first set of one or more signal metrics and a second set of signal metrics. The first set of signal metrics can be generated in response to the first chronic condition indicator meeting a first specified criterion, and the second set of signal metrics can be generated in response to the second chronic condition indicator meeting a second specified criterion. For example, the first set of signal metrics can include a five-day average of intracardiac impedance signal and a daily maximum respiration rate signal when the patient has a chronic condition of renal disease, and the second set of signal metrics can include a standard deviation of R-R intervals (such as acquired from an electrogram or a intracardiac electrogram signal) signal and a five-day average of transthoracic impedance signal when the patient has a chronic condition of diabetes. The signal metrics corresponding to the respective chronic condition indicator can be selected using the population-based information. Examples of the signal metrics generator circuit 223 are described below, such as with reference to FIG. 3.

The patient-specific signal metric selector circuit 224 can be configured to select one or more patient-specific signal metrics from the plurality of signal metrics generated by the signal metrics generator circuit 223. The patient-specific signal metrics can be used to estimate patient's risk of developing a future HF event such as an HF decompensation event. The patient-specific signal metrics can include one or more signal metrics selected from a group including both the first set of one or more signal metrics and the second set of one or more signal metrics. In an example, if there is at least one signal metric shared by the first and the second set of the signal metrics (i.e., the intersection of the first and the second sets of the signal metrics are not empty), the patient-specific signal metrics can include at least one signal metric from an intersection of the first set and the second set of signal metrics. In another example, the patient-specific signal metrics selector circuit can include at least one signal metric from the first set of signal metrics and at least one signal metric from the second set of signal metrics.

The HF risk stratification circuit 230 can receive input from the patient-specific signal metrics selector circuit 224 and can be configured to generate a composite risk index using the selected one or more patient-specific signal. The composite risk index can indicate the probability of the patient later developing an event indicative of worsening of HF, such as developing a future HF decompensation event within a specified timeframe, such as approximately 3-6 months, or more than 6 months. In various examples, the HF risk stratification circuit 230 can be configured to identify patients at elevated risk of developing a new or worsening of an existing disease, such as pulmonary edema, pulmonary condition exacerbation such as COPD, asthma and pneumonia, myocardial infarction, dilated cardiomyopathy (DCM), ischemic cardiomyopathy, systolic HF, diastolic HF, valvular disease, renal disease, chronic obstructive pulmonary disease (COPD), peripheral vascular disease, cerebrovascular disease, hepatic disease, diabetes, asthma, anemia, depression, pulmonary hypertension, sleep disordered breathing, hyperlipidemia, among others.

The controller circuit 240 can control the operations of the signal analyzer circuit 220 and the subcomponent circuits 221 through 224, the HF risk stratification circuit 230, and the data flow and instructions between these components. The controller circuit 240 can receive external programming input from the instruction receiver circuit 250 to control one or more of the receiving patient status, signal sensing, signal metrics generation, patient-specific signal metrics selection, or HF risk stratification. Examples of the instructions received by instruction receiver 250 may include: selection of electrodes or sensors used for sensing physiologic signals, selection of chronic conditions of the patient, or configuration of the HF risk stratification circuit 230. The instruction receiver circuit 250 can include a user interface configured to present programming options to the user and receive user's programming input. The instruction receiver circuit 250 can be coupled to the patient status input unit 221 to receive the patient chronic condition indicators such as via the user interface. In an example, at least a portion of the instruction receiver circuit 250, such as the user interface, can be implemented in the external system 120.

Figure 3:
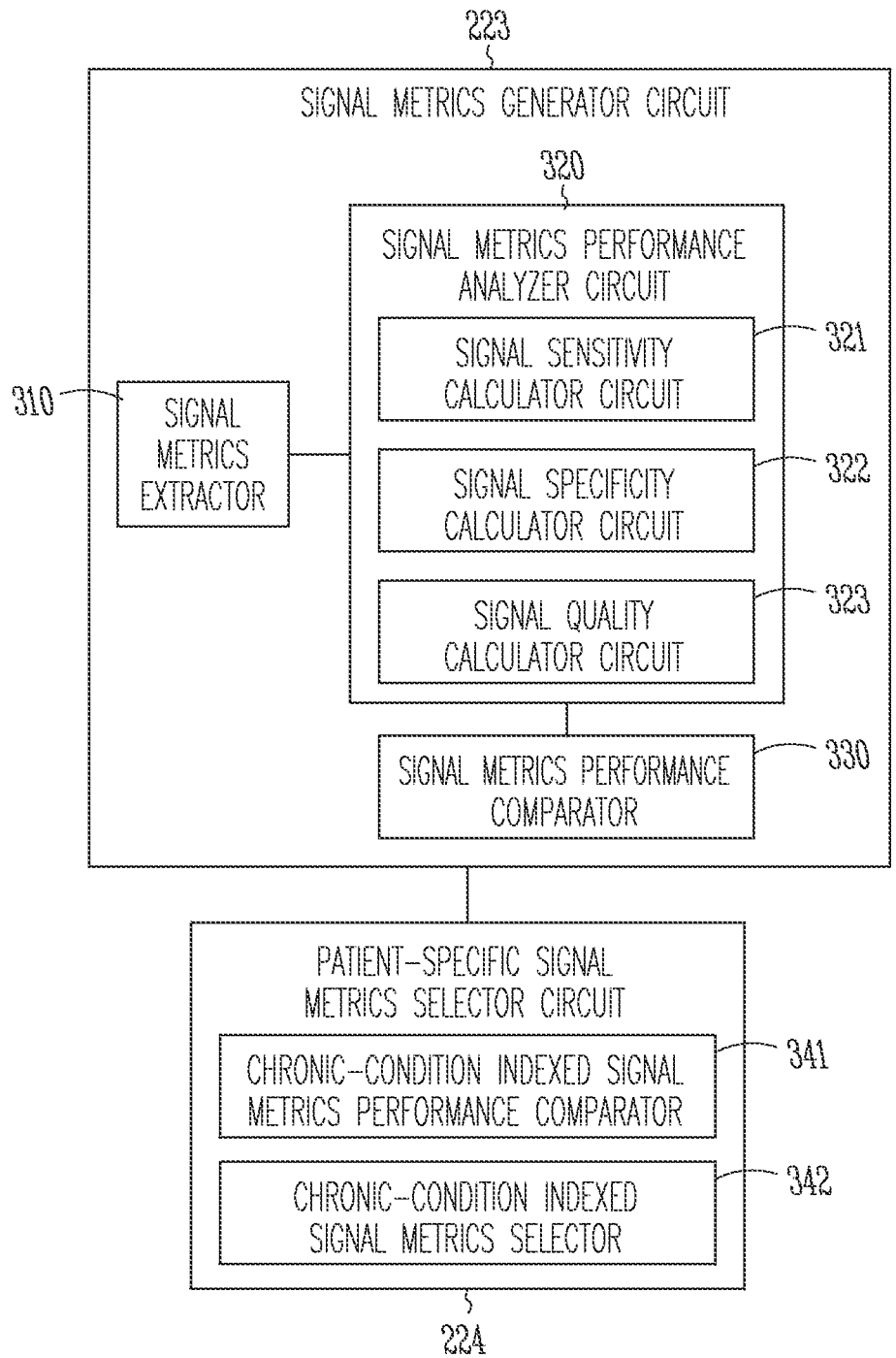
FIG. 3 illustrates an example of the signal metrics generator circuit.

FIG. 3 illustrates an example of the signal metrics generator circuit 300, which can be an embodiment of signal metrics generator circuit 223. The signal metrics generator circuit 300 can include one or more of a signal metrics extractor 310, a signal metrics performance analyzer circuit 320, and a signal metrics performance comparator 330.

The signal metrics extractor 310 can receive one or more processed physiologic signals sensed from the patient and extract signal features from the physiologic signals. The extracted signal metrics can include a statistical signal feature, a morphological signal feature, or a feature indicative of a physiologic activity. Examples of the extracted signal features can include mean, median, standard deviation, variance, correlation, covariance, or other statistical value over a specified time segment; peak, trough, slope, area under the curve of a sensor signal, P wave and QRS complexes in an electrogram signal, or S1, S2, S3 or S4 components of a heart sound signal, an inspiration phase and expiration phase of a respiration signal, among others.

The signal metrics extractor 310 can extract signal features when a patient chronic condition indicator such as that received by the patient status input unit 221 meets a specified condition. For example, when a patient chronic condition of having a chronic kidney disease is received by the patient status input unit 221, the signal metrics extractor 310 can extract signal features including daily maximum respiration rate (MRR), transthoracic impedance, and S3 heart sound amplitude. When two or more patient chronic condition indicators are received, the signal metrics extractor 310 can extract signal features for each of the patient chronic condition indicator. The association between a chronic condition indicator and the corresponding signal metrics can be stored in a machine-readable medium such as a memory device. The association can be created in a form of searchable data structure such as a lookup table or association map to facilitate automatic selection of time window. The data structure contains a plurality of chronic condition indicators or categorical classifications of one or more of the chronic condition indicators, each of which can be mapped to corresponding one or more signal metrics.

The signal metrics performance analyzer circuit 320 can be configured to generate, for one or more of the signal metrics from the signal metrics extractor 310, respective performance measures indicative of reliability or accuracy of predicting a risk of future HF event. As illustrated in FIG. 3, the signal metrics performance analyzer circuit 320 can include at least one of a signal sensitivity calculator circuit 321, a signal specificity calculator circuit 322, or a signal quality calculator circuit 323. Each of the calculator circuits 321 through 323 alone or in any combination can be used to evaluate the performance of the one or more signal metrics provided by the signal metrics extractor 310.

The sensitivity calculator circuit 321 can be configured to determine the sensitivity of a signal metric in response to a physiologic change associated with the progression of the HF status, such as using comparison of measurements of the signal metric at two non-identical states. The first and the second states can include non-identical temporal information. In an example, the sensitivity calculator circuit 321 can calculate for a signal metric (X) a relative change (such as a difference $\Delta X$) between the signal metric at a first state $(X_{S1})$ and the signal metric at the second state $(X_{S2})$, that is, $\Delta X = X_{S1} - X_{S2}$. The relative change can include a rate of change $(\Delta X/\Delta t)$ of the signal metric over the duration between the first and the second state, that is, $\Delta X/\Delta t = (X_{S1} - X_{S2})/(T_{S1} - T_{S2})$, where $T_{S1}$ and $T_{S2}$ respectively represents occurrence time of the first and the second states. In an example, $T_{S1}$ can be approximately 14-28 days prior to patient's developing a target event such as an HF decompensation event, and $T_{S2}$ can be a time preceding $T_{S1}$ by specified time duration of approximately 1-6 months or approximately 1-3 months. The second state can be a baseline state representing the historical trend of the signal metric when the patient does not develop the target event. The signal metric at the baseline state can be computed using a linear or nonlinear combination of a plurality of historical measurements of the signal metric. The relative change in the signal metric from the first state (such as the state prior to an HF decompensation event) to the second state (such as a state preceding the first state or a baseline state) thus can indicate predictive content in the signal metric in response to the progression of HF status. A signal metric with high sensitivity preserves high predictive content in identifying a future risk of developing an event of worsening HF, such as an HF decompensation event. In an example, the sensitivity calculator circuit 321 can calculate a statistical significance of relative change $\Delta X$ or $\Delta X/X_{S2}$. The significance can be computed as a p-value obtained by fitting relative change data from a group of patients to a statistical model. The sensitivity of a signal metric can be computed using both the p-value as discussed above and the relative change $\Delta X$ or $\Delta X/X_{S2}$. A signal metric having a large and significant change, such as large $\Delta X$ or $\Delta X/X_{S2}$ and small p value, is more desirable for detecting a target event such as a HF decompensation event. In an example, a sensitivity score can be computed as a product of a relative change $\Delta X/X_{S2}$ and a negative logarithm of the p-value, i.e., $-\log(\text{p-value})*\Delta X/X_{S2}$. A higher sensitivity score preserves high predictive content in detecting the target event.

The specificity calculator circuit 322 can be configured to determine the specificity of a signal metric in response to a physiologic or non-physiologic change not associated with the worsening of HF. For example, in predicting a likelihood of future HF decompensation event, confounding events such as noise, inference, patient activity, lead fracture, lead revision, change of pacing configuration, or a replacement of the device are not physiologic changes associated with an impending HF decompensation event. The specificity can characterize the accuracy of the signal metric in predicting an event not due to worsening of HF. The specificity calculator circuit 322 can determine the specificity using comparison of measurements of the signal metric at two non-identical states. The first and the second states can include non-identical temporal information. The specificity calculator circuit 322 can calculate a relative change in a signal metric (X) from a first state to a second state. The first state can occur at a time such as approximately 14-28 days prior to patient's developing a target event such as an HF decompensation event. The second state can occur at a time preceding the first state by at least specified time duration, such as approximately 1-6 months or approximately 1-3 months. The second state can be a baseline state representing the historical trend of the signal metric. The relative change in the signal metric from the first state (such as the state prior to an HF decompensation event) to the second state (such as a state preceding the first state or a baseline state) thus can indicate response of the signal metric in the absence of events indicative of worsening of HF. A signal metric with high specificity therefore reduces the rate of false prediction of a low-risk event as a high-risk event.

The signal quality calculator circuit 323 can be configured to determine the signal quality of the signal metric. Signal quality can include signal strength, signal variability, or signal-to-noise ratio, among others. Examples of the signal variability can include range, inter-quartile range, standard deviation, variance, sample variance, or other first-order, second-order, or higher-order statistics representing the degree of variation. For example, in determining the quality of a signal metric of S1 heart sound intensity, the signal quality calculator circuit 323 can perform a plurality of measurements of the S1 heart sound intensity such as from a plurality of cardiac cycles during a specified period of time. The signal quality calculator circuit 323 can determine the variability of the S1 intensity by computing a variance of the plurality of measurements of the S1 intensity. A high signal quality, such as indicated by one or more of a high signal-to-noise ratio, a high signal strength, or a low signal variability, is desirable for identifying patients at the elevated risk of developing future HF events.

The signal sensitivity calculator circuit 321, the signal specificity calculator circuit 322, or the signal quality calculator circuit 323 can determine respective signal performance measures (e.g., signal sensitivity, specificity, or quality) using population-based statistics. For example, the signal metric of daily maximum respiration rate (MRR) can be measured in a cohort of patients with the chronic condition (such as renal disease) identical or similar to the present patient. Statistics such as the signal sensitivity, signal specificity, or signal quality with regard to the population-based daily MRR can be determined from the population-based data. These statistical data can be retrieved from a database or otherwise provided to the signal metrics performance analyzer circuit 320 and used by one or more of the signal sensitivity calculator circuit 321, the signal specificity calculator circuit 322, or the signal quality calculator circuit 323. In an example, the signal metrics performance analyzer circuit 320 can determine respective signal performance measures using both the population-based statistics (e.g., population-based sensitivity of daily MRR) and the performance measure of the patient (e.g., sensitivity of daily MRR).

The signal metrics performance comparator 330 can be coupled to the signal metrics performance analyzer circuit 320, and configured to select one or more signal metrics from a plurality of signal metrics based at least in part on a comparison of the performance measures including the signal sensitivity, the signal specificity, or the signal quality, or any combination thereof. In an example, the signal metrics performance comparator 330 can compute a composite performance score for a signal metric using a linear combination or nonlinear combination of one or more of performance measures. The composite performance score can then be compared to a specified threshold to determine whether the signal metric can be selected. For example, a composite performance score ($F_{MRR}$) for the signal metric of daily maximum respiration rate (MRR) can be computed as $F_{MRR}=a*Ss+b*Sp+c*Q$, where a, b, c are scalar weights to respective performance measures sensitivity (Ss), specificity (Sp), and quality (Q). The signal metrics performance comparator 330 can select daily MRR as a sensor-based "risk stratifier" for predicting the likelihood of future HF decompensation event if $F_{MRR}$ exceeds a specified threshold, e.g., $F_{MRR}>F_{MRR-TH}$. In another example, the signal metrics performance comparator 330 can select the signal metric when one or more performance measures meet specified criteria. For example, the signal metrics performance comparator 330 can select daily MRR for identifying patient's risk of developing future HF decompensation event if sensitivity, specificity, or quality each exceeds respective threshold, e.g., $Ss>Ss_{TH}$, $Sp>Sp_{TH}$, or $Q>Q_{TH}$.

When the signal metrics extractor 310 generates more than one signal metrics are provides them to the signal metrics performance analyzer circuit 320, the signal metrics performance comparator 330 can organize the signal metrics such as prioritizing the signal metrics. The signal metrics performance comparator 330 can prioritize the signal metrics based at least in part on their respective performance measures. For example, corresponding to a chronic condition indicator of patient having diabetes, the signal metrics extractor 310 can generate a set of signal metrics including standard deviation of average normal RR interval (SDANN), 24-hour max intracardiac impedance (Zmax), daily maximum of respiration rate (MRR), and daily maximum of tidal volume (TV). The signal metrics performance analyzer circuit 320 can compute composite performance score (F) for each of the signal metrics. If the comparison of the performance measures at the signal metrics performance comparator 330 indicates that $F_{MRR} \geq F_{TV} \geq F_{Zmax} \geq F_{SDANN}$, then the prioritized signal metrics can be in the order of (MRR, TV, Zmax, SDANN).

The patient-specific signal metrics selector circuit 224 can be coupled to the signal metrics generator circuit 223 and receive therein at least a first set of one or more signal metrics corresponding to the first chronic condition indicator and a second set of signal metrics corresponding to the second chronic condition indicator. The patient-specific signal metrics selector circuit 224 can include a chronic-condition indexed signal metrics performance comparator 341 and a chronic-condition indexed signal metrics selector 342. The chronic-condition indexed signal metrics performance comparator 341 can compare the signal metrics in the first set to the signal metrics in the second set, such as to identify one or more common signal metrics shared by the first and the second sets of the signal metrics. The chronic-condition indexed signal metrics performance comparator 341 can also compared the performance measures such as the signal sensitivity, specificity, or signal quality of the signal metrics in the first and the second sets.

The chronic-condition indexed signal metrics selector 342 can be configured to select from the plurality of signal metrics one or more patient-specific signal metrics selected from a group including both the first set of one or more signal metrics and the second set of one or more signal metrics. In an example, the chronic-condition indexed signal metrics selector 342 can select at least one signal metric from an intersection of the first set and the second set of signal metrics, where the intersection includes at least one common signal metric shared by both the first and the second set of signal metrics. The chronic-condition indexed signal metrics selector 342 can select at least one signal metric from the first set of signal metrics and at least one signal metric from the second set of signal metrics. For example, the chronic-condition indexed signal metrics selector 342 can use the prioritized signal metrics such as provided by the signal metrics performance comparator 330, and select a signal metric with the highest composite performance from the first set, and a signal metric with the highest composite performance score from the second set. Other approaches of selecting patients-specific signal metrics from the first and the second sets based at least in part on the performance measures have also been contemplated.

Figure 4:
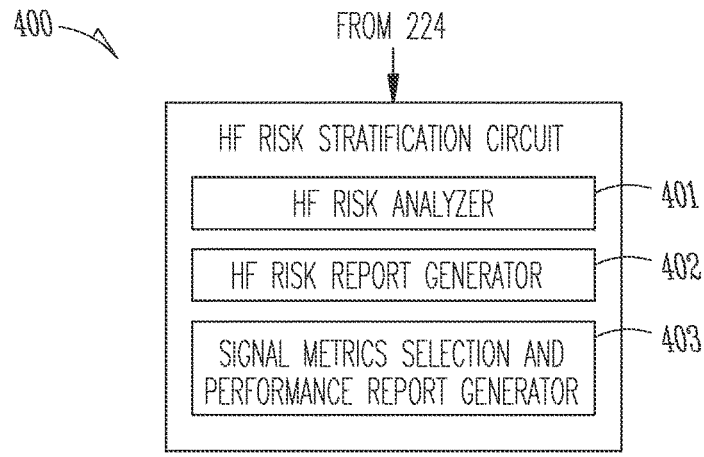
FIG. 4 illustrates an example of HF risk stratification circuit.

FIG. 4 illustrates an example of HF risk stratification circuit 400, which can be an embodiment of the HF risk stratification circuit 230. The HF risk stratification circuit 400 can receive the chronic-condition indexed signal metrics from the patient-specific signal metrics selector circuit 224, and generate a composite risk index (CRI) using the received signal metrics. The CRI can be a quantity that indicates the probability of the patient later developing an event indicative of worsening of HF. In an example, the worsening of HF can be an event indicative of HF decompensation status. The HF risk stratification circuit 400 can include an HF risk analyzer 401, an HF risk report generator 402, and a signal metrics selection and performance report generator 403.

The HF risk analyzer 401 can generate a CRI using the chronic-condition indexed signal metrics. The HF risk analyzer 401 can generate for each of the chronic-condition indexed signal metric (Mi) a respective individual risk score ($R_{Mi}$) using a specified probability model. The HF risk analyzer 401 can compute the composite risk index using a linear or nonlinear combination of the risk scores associated with respective chronic-condition indexed signal metrics. The weight factor can be proportional to the performance measure of the respective signal metric. For example, if the patient-specific signal metrics selector circuit 224 selects MRR and SDANN according the patient chronic conditions, and the respective performance measures are $F_{MRR}$ and $F_{SDANN}$, and the respective individual risk score is $R_{MRR}$ and $R_{SDANN}$, then the CRI can be computed as $CRI=R_{MRR}*F_{MRR}/(F_{MRR}+F_{SDANN})+R_{SDANN}*F_{SDANN}/(F_{MRR}+F_{SDANN})$. The CRI an also be determined as a parametric or non-parametric models using the individual risk index, such as decision trees, neural network, Bayesian network, among other machine learning methods. In an example, the CRI can be computed using a probability model $p(D)=1/(1+exp(x))$, where p(D) represents a probability of the target event such as a HF decompensation (D) event, and x represents a linear or nonlinear combination of individual risk scores, or a linear or nonlinear combination of measurements of the selected one or more patient-specific signal metrics.

The HF risk analyzer 401 can generate two or more categorical risk levels using a comparison between the CRI and a reference measure. The reference measure can be computed using the chronic-condition indexed signal metrics of a patient population. A higher degree of dissimilarity between the CRI and the reference can indicate a higher risk of the patient developing HF events in the future than an average patient with the similar chronic conditions. Examples of HF risk stratification using the chronic-condition indexed signal metrics are discussed below, such as with reference to FIG. 7.

The HF risk report generator 402 can generate a report to inform, warn, or alert the user the elevated risk of patient's developing a future HF event. The report can include one or more composite risk indices with corresponding timeframe within which the risk is predicted. The report can also include recommendations actions such as confirmative testing, diagnosis, or treatment options. The report can include one or more formats of media including, for example, a textual or graphical message, a sound, an image, or a combination thereof. In an example, the HF risk report generator 402 can be coupled to the instruction receiver circuit 250 and the report can be presented to the user via an interactive user interface on the instruction receiver circuit 250. The HF risk report generator 402 can be coupled to the external device 120, and be configured to present to the user the risk (such as the composite risk index) of patient developing future HF events via the external device 120.

The signal metrics selection and performance report generator 403 can generate, and present to the user, one or more of a report including the chronic condition indicators such as received from the patient status input unit 221, signal metrics and the respective performance measures such as generated by the signal metrics generator circuit 223, or the chronic-condition indexed signal metrics such as generated by the patient-specific signal metrics selector circuit 224. The signal metrics selection and performance report generator 403 can be coupled to the external device 120 or the instruction receiver circuit 250, and be configured to present the signal metrics information to the user therein. The user input can include confirmation, storage, or other programming instructions to operate on the patient-specific signal metrics or patient chronic condition indicators.

Figure 5:
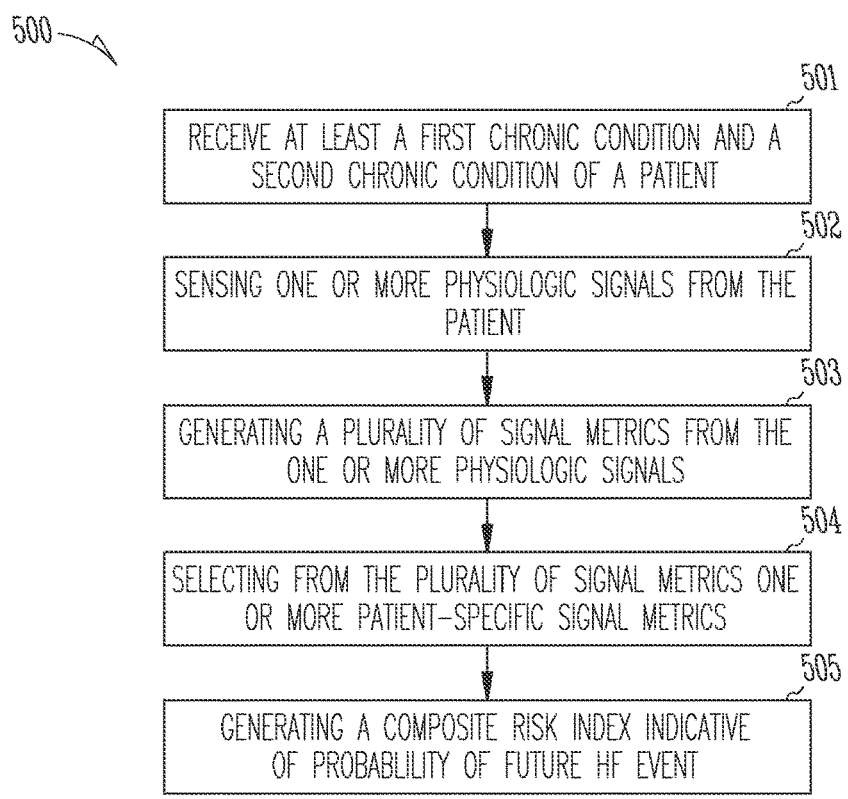
FIG. 5 illustrates an example of a method for risk stratification for future HF event.

FIG. 5 illustrates an example of a method 500 for predicting a risk of future HF event such as HF decompensation event using one or more physiological signals. The method 500 can be implemented and operate in an ambulatory medical device or in a remote patient management system. In an example, the method 500 can be performed by the patient chronic condition-based HF risk assessment circuit 113 implemented in IMD 110, or the external device 120 which can be in communication with the IMD 110.

At 501, at least two chronic condition indicators of a patient can be received. The patient chronic condition indicators can be descriptive of the patient characteristics or sustained medical status that do not change or slowly change over a certain specified time, such as approximately at least six months. The at least two chronic condition indicators, including a first and a second chronic condition indicator of the patient, can be non-identical. For example, the first and the second chronic condition indicators can respectively include at least one of a chronic disease indicator of the patient (e.g., prior MI, ischemic or dilated cardiomyopathy, valvular disease, renal disease, COPD), a prior medical procedure indicator of the patient (e.g., CABG, thoracic surgery), or a demographic characteristic indicator of the patient (e.g., age, sex, race, height, NYHA classifications). The chronic condition indicators can include binary values indicating the presence or absence of a specified condition, a plurality of categorical classifications or progressive stages of a particular chronic condition, or a plurality of value ranges of a physiologic parameter.

At 502, one or more physiological signals can be sensed from the patient. The physiological signal may represent electrical or mechanical activities in the body. Examples of the physiological signal include: heart rate, heart rate variation, conduction times, arrhythmias, intrathoracic impedance, intracardiac impedance, arterial pressure, pulmonary artery pressure, RV pressure, LV coronary pressure, heart sounds, respiration signals including respiration rate or tidal volume; coronary blood temperature, blood oxygen saturation, electrolyte concentrations, or other measures descriptive of the patient's physiology. The physiological signal can be received from a signal sensing circuit coupled to the electrodes on one or more of the leads such as 108A-C, or implanted or external physiologic sensors associated with an ambulatory medical device. The physiologic signal can also be received from a signal memory where the physiological data are stored.

At 503, a plurality of signal metrics can be generated from the one or more physiologic signals. A signal metric can include signal feature extracted from the one or more physiologic signals, such as a statistical measure, a morphologic measure, or a portion of the physiologic signal indicative of a physiologic activity. Examples of the signal metrics can include: mean, median, or other central tendency of a portion of a physiologic signal; variance, standard deviation, or other second-order or higher-order statistical measure of a portion of a physiologic signal; peak, trough, slope or other morphological features of a portion of a physiologic signal; P wave and QRS complexes in an electrogram signal; S1, S2, S3 or S4 components of a heart sound signal; inspiration phase and expiration phase of a respiration signal.

The generated signal metrics can include a first set of one or more signal metrics when the first chronic condition indicator meets a first specified criterion, and a second set of one or more signal metrics when the second chronic condition indicator meets a second specified criterion. Since the first and the second chronic condition indicators can be non-identical to each other, the first set of the signal metrics may not be identical to the second set of signal metrics. In an example, the first chronic condition indicator is CKD and the second chronic condition indicator is diabetes. When the first chronic condition indicator meets the criterion of "CKD of stage 3 or above", the first set of signal metrics ($M_{CKD}$) can include: $M_{CKD}$={daily maximum respiration rate signal (MRR), average of intracardiac impedance signal (AvgZ1), S3 heart sound amplitude (S3Amp)}. When the second chronic condition indicator meets the criterion of "patient having diabetes within the past 5 years", the second set of signal metrics ($M_{Diabetes}$) can include: $M_{Diabetes}$={standard deviation of average R-R intervals (SDANN), average of intracardiac impedance signal (AvgZ1)}. Examples of the selection of signal metrics in accordance with the patient chronic condition indicator is discussed below, such as with reference to FIG. 6.

At 504, one or more patient-specific signal metrics can be selected from the plurality of signal metrics such as generated at 503. The patient-specific signal metrics can includes at least one signal metric from an intersection of the first set of signal metrics corresponding to the first chronic condition indicator and the second set of signal metrics corresponding to the second chronic condition indicator. In an example where the first set of signal metrics corresponding to CKD includes $M_{CKD}$={MRR, AvgZ1, S3Amp} and the second set of signal metrics includes $M_{Diabetes}$={SDANN, AvgZ1}, the intersection of the two sets $M_{CKD}$ and $M_{Diabetes}$, namely AvgZ1, can be selected as the patient-specific signal metrics, that is, $M_p$={AvgZ1}. In another example, the patient-specific signal metrics can include at least one signal metric from the first set of signal metrics and at least one signal metric from the second set of signal metrics. Using the example of $M_{CKD}$ and $M_{Diabetes}$ as discussed above, the patient-specific signal metrics can be selected as $M_p$={MRR, SDANN}. The selection of the signal metric from each set to be a patient-specific signal metrics can be performed using performance measure of respective signal metrics in each set. Examples of the performance measure of the signal metrics is discussed below, such as with reference to FIG. 6.

At 505, a composite risk index (CRI) can be generated using the selected patient-specific signal metrics, such as that determined at 504, to estimate a probability of the patient developing a future HF event, such as an event indicative of HF decompensation status of the patient. The CRI can be computed using risk scores associated with the one or more patient-specific signal metrics. For example, the CRI can be a linear or nonlinear function of the risk scores. The risk scores indexed by the first and the second chronic condition indicators can be computed using a probabilistic model created using population-based data. Examples of generating the risk scores for the chronic-condition indexed signal metrics is discussed below, such as with reference to FIG. 7.

The computed CRI can be further categorized into two or more risk levels indicating elevated risk of the patient later developing the HF event. The CRI can be compared to a reference measure, and the dissimilarity between the CRI and the reference measure can be used to estimate the risk of future HF events.

Figure 6:
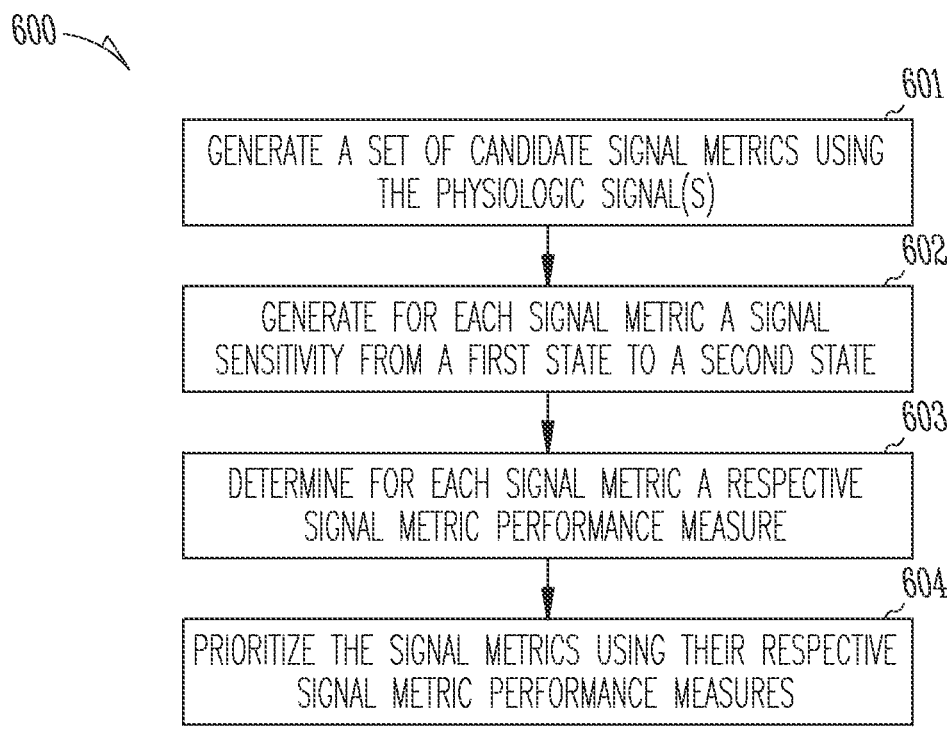
FIG. 6 illustrates an example of a method for generating signal metrics from physiologic signals.

FIG. 6 illustrates an example of a method 600 for generating a plurality of signal metrics from the one or more physiologic signals. The method 600 can be an example of 503. The method can take the input of a plurality of chronic condition indicators including at least a first and a second chronic condition indicators from a patient and one or more physiologic signals sensed from the patient such as using one or more physiologic sensors, and generate a set of signal metrics corresponding to each respective chronic condition indicator. The method 600 can also generate performance measure of each signal metric, which can be used to select one or more patient-specific signal metrics such as at 504. In an example, the method 600 can be performed by the signal metrics generator circuit 223 as illustrated in FIG. 2.

At 601, for each received chronic condition indicator, a respective set of candidate signal metrics can be generated when the chronic condition indicator meets a specified criterion, such as being categorized as a specified class of status, stage of disease, or a value range of a physiologic parameter. The candidate signal metrics associated with each chronic condition indicator, including the number, type, or methods of generating the candidate signal metrics, can be pre-determined such as using the population-based data. For example, for patient with CKD of stages 3 or above, various signal metrics can be evaluated in a cohort of patients with the similar chronic condition (e.g., CKD of stage 3 or above) and another cohort of patients absent of similar chronic condition. If a signal metric (e.g. daily maximum respiration rate, or MRR) shows a desirable level of difference between the two cohorts of patients, then the signal metric can be determined as a candidate signal metric associated with the chronic condition of CKD.

At 602, a signal sensitivity measure can be generated for each candidate signal metric. A sensitivity measure can be indicative of the ability of a signal metric in predicting a progression of a target event or condition. The sensitivity measure can be computed as a relative change of the respective signal metric from a first state to a second state. In an example, the second state includes temporal information non-identical to that of the first state. For example, in predicting the risk of future HF decompensation event, the first state can occur at a time prior to patient's developing a target event such as an HF decompensation event, and the second state can occur at a time preceding the first state by at least a specified time duration, such as approximately 1-6 months or approximately 1-3 months. In another example, the second state can be a baseline state computed using a plurality of historical measurements of the signal metric. The sensitivity measure can include a false negative rate of detecting a target event or condition. A low false negative rate can correspond to a high sensitivity measure. The sensitivity measure can also include a positive predictive value (PPV) which represents likelihood of correctly recognizing a target event or condition. A signal metric with high sensitivity preserves predictive content in predicting the risk of future HF event such as an HF decompensation event.

The computed signal sensitivity measure can be used to determine a performance measure for the respective signal metric at 603. The performance measure can indicate how well the signal metric can predict the worsening of HF. In an example, the performance measure can include the sensitivity measure of the signal metric and the population-based statistics of the signal metrics. While the sensitivity measure can include "intra-patient" relative change of the signal metrics between two states with non-identical temporal information, the population-based statistics can include "inter-patient" consistency of the signal metric in preserving the predictive content in estimating the risk of future HF event. For example, population-based statistics, such as average, variance, or statistical distribution of the sensitivity measure of daily MRR across a cohort of patients with similar type of chronic condition (e.g., CKD of stage 3 and above), can be retrieved from the patient database, and further be used in determining the performance measure.

The performance measure for the respective signal metric can be determined using other parameters either in conjunction with or as an alternative to the sensitivity measure of the respective signal metric. In one example, the performance measure can include a specificity measure of a signal metric in response to a physiologic or non-physiologic change not associated with the target event or condition such as worsening of HF or HF decompensation event. The specificity measure can be calculated a relative change in a signal metric from a first state (such as the state prior to an HF decompensation event) to the second state (such as a state preceding the first state or a baseline state) in the absence of the target event. The specificity measure can include a false positive rate of detecting a target event or condition. A low false positive rate can correspond to a high specificity measure. The specificity measure can also include a negative predictive value (NPV) which represents likelihood of correctly recognizing a non-target event or condition. In another example, the performance measure can include a signal quality measure such as signal strength, signal variability, or signal-to-noise ratio. In various examples, population-based statistics of the specificity measure or of the signal quality measure, such as central tendency or statistical distribution computed using data of a cohort of patients with similar type of chronic condition, can be retrieved from a database and used in determining the performance measure.

At 604, candidate signal metrics with respect to each chronic condition indicator input can be compared and prioritized using at least their respective performance measures. In an example, for each candidate signal metric, a composite performance score can be computed such as a linear combination or nonlinear combination of one or more of the sensitivity measure, the specificity measure, or the signal quality measure. The candidate signal metrics with respect to each chronic condition indicator can be prioritized such as being organized in a descending order at least based on the their respective composite performance scores. The prioritized candidate signal metrics and the respective composite performance scores can be to select one or more patient-specific signal metrics such as at 504.

Figure 7:
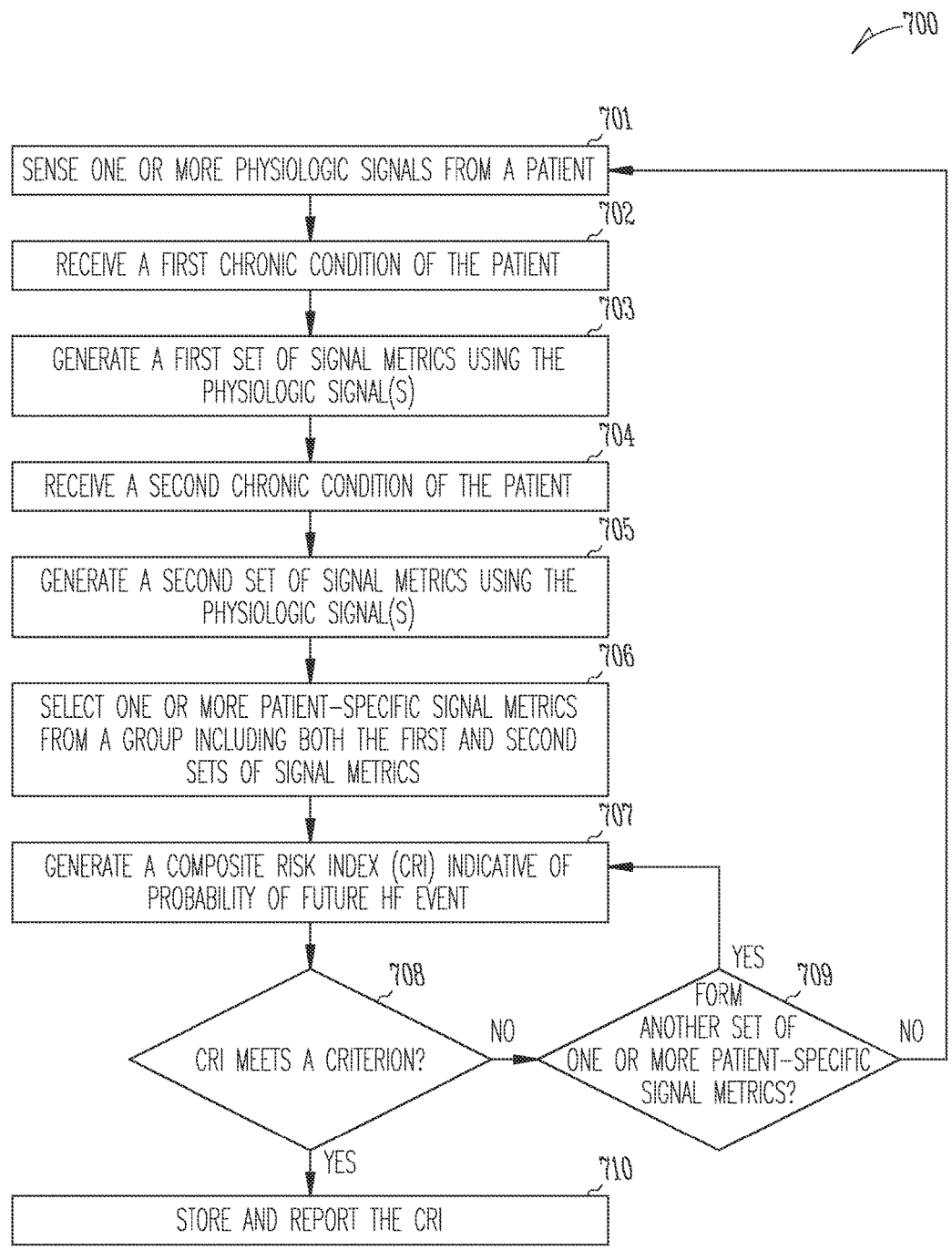
FIG. 7 illustrates an example of a method for providing a risk stratification of a future HF event.

FIG. 7 illustrates an example of method 700 for providing a risk stratification of a future HF event using one or more physiological signals such as using information of the patient chronic condition indicators. The method 700 can be an embodiment of the method 500. In an example, the method 700 can be performed by the patient chronic condition-based HF risk assessment circuit 200.

At 701, one or more physiological signals of a patient can be received. The physiologic signals may be received from a signal sensing circuit coupled to electrodes or external or implanted physiologic sensors associated with an ambulatory medical device or a physiological monitor, or from a signal memory.

At 702, a first chronic condition indicator of the patient can be received such as from a system user (e.g., a physician) via a user interface on a transceiver in communication with the ambulatory medical device. The chronic condition indicator can include a chronic disease indicator of the patient, a prior medical procedure indicator of the patient, a demographic characteristic indicator of the patient, or any other condition descriptive of the patient characteristics or sustained medical status that do not change or slowly change over a certain specified time, such as approximately at least six months. The first chronic condition indicator can be compared to a specified criterion at 703, such as determining if the first chronic condition indicator falls under a categorical class or a progressive stage of a chronic disease. When the first chronic condition indicator meets the specified criterion, a first set of signal metrics can be generated using the one or more physiologic signals at 703. The signal metrics can be generated according to specified instructions and methods stored in the ambulatory medical device. For each signal metric a respective performance measure can be computed, which includes a sensitivity, a specificity, a signal quality measure such as the signal-to-noise ration of the signal metric, or any combination thereof.

At 704, a second chronic condition indicator of the patient can be received. The second chronic condition indicator can be non-identical to the first chronic condition indicator. A second set of signal metrics can be generated at 705 using a similar approach of signal metrics generation for the first chronic condition indicator at 703. Because the second chronic condition indicator is not identical to the first chronic condition indicator, the second set of signal metrics can be non-identical to the first set of signal metrics.

At 706, one or more patient-specific signal metrics can be selected from a group including both the first and second sets of signal metrics. In an example, if there is at least one signal metric shared by the first and the second set of the signal metrics, the patient-specific signal metrics can include at least one signal metric from an intersection of the first set and the second set of signal metrics. Alternatively or additionally, the patient-specific signal metrics can include at least one signal metric from the first set of signal metrics and at least one signal metric from the second set of signal metrics. For example, the signal metrics with respect to each chronic condition indicator can be organized according to their respective performance measure. The patient-specific signal metrics can include the signal metric with the highest performance measure from the first set and the signal metric with the highest performance measure from the second set.

At 707, a composite risk index (CRI) can be generated using the one or more patient-specific signal metrics. The CRI can be a quantity that indicates the probability of the patient later developing an event indicative of worsening of HF, such as excessive intrathoracic fluid accumulation, increased heart sounds, increased heart rate, increased respiratory rate, decreased tidal volume, reduction in activity, or other events indicative of HF decompensation status.

For each patient-specific signal metric selected at 706, a respective individual risk score can be computed such as using a probability model. For example, the individual risk score ($R_{Mi}$) can be computed as posterior probability of the patient developing a future HF event (E) given the measurement of the signal metric (Mi), i.e., $R_{Mi}=P(E|M_i)$. The posterior probability can be computed using the Bayes theorem $R_{Mi}=P(Mi|E)*P(E)/P(Mi)$ where $P(Mi|E)$ is the likelihood and $P(E)$ the prior probability. The likelihood $P(Mi|E)$ can be generated using population-based data.

The composite risk index (CRI) at 707 can be computed using a linear or nonlinear combination of at least a portion of the risk scores with respect to the chronic-condition indexed signal metrics. For example, assume that three signal metrics indexed by the patient chronic condition of chronic kidney disease (CKD) of stage 3 or above are represented by $M_{CKD}=\{MRR, AvgZ1, S3Amp\}$. The respective risk scores with these signal metrics can be denoted as $R_{MRR}$, $R_{AvgZ1}$, and $R_{S3Amp}$. Then CRI can be computed as a function of the respective risk scores such that $CRI=f(R_{MRR}, R_{AvgZ1}, R_{S3Amp})$. The risk integration function $f$ can be a linear function, such that the CRI can be computed as weighted sum of the individual risk scores, that is, $CRI=a*R_{MRR}+b*R_{AvgZ1}+c*R_{S3Amp}$, where a, b, and c are weight factors assigned to the respective risk scores. The weight factors can be pre-determined scalars such as stored in a memory where it can be read for use. The weight factors can also be determined using the signal metrics performance measures such as determined for the one or more patient-specific signal metrics at 706. In an example, the weight factor for a particular risk score can be determined as a quantity proportional to the performance measure of the respective signal metric. In an example, the CRI can be computed using a probability model $p(D)=1/(1+exp(x))$, where p(D) represents a probability of the target event such as a HF decompensation (D) event, and x represents a linear or nonlinear combination of individual risk scores, or a linear or nonlinear combination of measurements of the selected one or more patient-specific signal metrics.

The risk integration function $f$ can be a nonlinear function, such as a nonlinear multivariate model. In some examples, the integration function $f$ can represent a computation method including a probability network such as a Bayesian network. At 707, a joint risk score can be computed in addition to the individual risk score. The joint risk score can indicate a posterior probability of the patient having a future HF event given the joint measurements of two or more chronic-condition indexed signal metrics. For example, the HF risk analyzer 401 can compute a joint risk score $R_{(Mi,Mj)}$, which can be computed as $R_{(Mi,Mj)}=P(E|(Mi, Mj))=P((Mi, Mj)|E)*P(E)/P(Mi, Mj)$. The likelihood $P((Mi, Mj)|E)$ can be determined using population-based data. Using the previous example of $M_{CKD}=\{MRR, AvgZ1, S3Amp\}$, the CRI can be computed as a function of individual risk scores and joint risk scores, i.e., $CRI=f(R_{MRR}, R_{AvgZ1}, R_{S3Amp}, R_{(MRR, AvgZ1)}, R_{(MRR, S3Amp)}, R_{(AvgZ1, S3Amp)}, R_{(MRR, AvgZ1)})$. The integration function $f$ can be probability network such as a Bayesian network.

At 708, the CRI is checked against a specified criterion, such as a reference or threshold value, to determine the risk of the patient developing a future HF event. The reference measure can be computed using the chronic-condition indexed signal metrics of a patient population. A plurality of patients of the patient population can have at least the first and the second chronic conditions indicators as the patient under analysis. The reference measure computed from such a population can indicate an "average" patient's risk of developing future HF events. The reference measures can include: the mean, median, a range, or other central tendency of the risk across the patient population; variance, standard deviation, or other second or higher order statistical measures across the patient population; histogram, statistical distribution, or the parametric or non-parametric model representing the histogram or statistical distributions.

The comparison can include computing a dissimilarity between the CRI and the reference. Examples of the dissimilarity can include a difference, a ratio, a percentile change, or other relative change. The dissimilarity can be computed as multi-dimensional distance using the statistical distribution of the reference measure. The dissimilarity can be compared to one or more thresholds such that the CRI can be categorized to two or more categorical risk levels indicating elevated risk of the patient later developing the HF event. For example, the categorical levels can include "high risk", "medium risk", or "low risk." A higher degree of dissimilarity between the CRI and the reference can indicate a higher risk of the patient developing HF events in the future than an average patient with the similar chronic conditions.

If the CRI meets the specified criterion such as the CRI value being categorized as "medium risk" or "high risk" level, then at 710 a report is generated to inform the user the elevated risk for the patient. The report can include any or all of the information of the patient-specific signal metrics selected for analysis, the CRI, the categorical classifications of CRI, or recommendations for intervention, further testing, or treatment options for the patient. The report can be in a form of a textual or graphical message, a sound, an image, or any combination thereof.

If the CRI does not meet the specified criterion, then at 709 a decision is made as to whether a new set of patient-specific signal metrics is to be used for computing a CRI. The new set of the patient-specific signal metrics can be different than the patient-specific signal metrics used at 706. For example, if at 706 the patient-specific signal metrics include only the intersection between the first set of signal metrics such as generated at 703 and the second set of signal metrics such as generated at 705, then at 709 the patient-specific signal metrics can include the signal metric with the highest performance score from the first set and the signal metric with the highest performance score from the second set. In another example, if at 706 the patient-specific signal metrics include the signals metrics with the highest performance score from the first and the second sets, then at 709, the patient-specific signal metrics can include the signals metrics with the second highest performance score from the first and the second sets. The decision at 709 can be received from a system user, or automatically executed in response to the CRI failing to meet the criterion (e.g., falling below a threshold) by a narrow margin. If a different set of patient-specific signal metrics is decided to be used, then a new CRI can be generated at 707; otherwise, the patient is deemed at low risk of developing future HF event; and no preventive action is deemed necessary. The patient monitoring can be continued with receiving the physiological signals at 701.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A medical device, comprising:
 a signal analyzer circuit, including:
  a patient status input unit configured to receive at least a first demographic characteristic indicator and a second demographic characteristic indicator of a patient, the second demographic characteristic indicator non-identical to the first demographic characteristic indicator;
  a signal receiver circuit configured to receive one or more physiologic signals of the patient;
  a signal metrics generator circuit configured to generate a plurality of signal metrics from the one or more physiologic signals, including to generate a first set of one or more signal metrics in response to the first demographic characteristic indicator meeting at least one first specified criterion, and to generate a second set of signal metrics in response to the second demographic characteristic indicator meeting at least one second specified criterion; and a patient-specific signal metric selector circuit configured to select a subset of patient-specific signal metrics from the first and second sets of signal metrics using signal metric performance measures of at least one metric from the first and second sets of signal metrics; and a risk stratification circuit configured to generate a composite risk index using the selected subset of patient-specific signal metrics, the composite risk index indicative of the probability of the patient later developing an event indicative of worsening of heart failure, the risk stratification circuit comprising a risk report generator configured to generate a report to inform a user of an elevated risk of the patient developing the event indicative of worsening of heart failure.

2. The device of claim 1, wherein the risk stratification circuit is configured to generate a composite risk index indicative of the probability of the patient developing a heart failure decompensation event within a specified timeframe.

3. The device of claim 1, wherein the patient status input unit is configured to receive a first chronic disease indicator and a second chronic disease indicator of the patient, wherein the signal metrics generator circuit is configured to generate the first set of signal metrics further based on the first chronic disease indicator, and to generate the second set of signal metrics further based on the second chronic disease indicator.

4. The device of claim 1, wherein:
the signal receiver circuit is configured to be coupled to at least one physiologic sensor configured to sense the one or more physiologic signals from the patient;
the signal metrics generator circuit comprises a signal metrics performance analyzer circuit configured to generate, for the first and second sets of signal metrics, respective signal metrics performance measures selected from the group consisting of a signal quality measure, a signal sensitivity measure, and a signal specificity measure; and
the patient-specific signal metrics selector circuit is configured to select the subset of patient-specific signal metrics based on the respective signal metric performance measures.

5. The device of claim 4, wherein the signal metrics performance analyzer circuit is configured to generate a sensitivity of a daily maximum respiration rate (MRR) indicative of a relative change from a baseline daily MRR, and wherein the signal metrics generator circuit is configured to generate a set of signal metrics including the daily MRR when the patient has no prior renal disease.

6. The device of claim 1, wherein the risk stratification circuit is configured to generate for each metric in the subset of patient-specific signal metrics respective risk scores using the first or second demographic characteristic indicators, and to calculate the composite risk index using the respective risk scores.

7. The device of claim 6, wherein the risk stratification circuit is configured to calculate the composite risk index using a weighted function of the risk scores for the subset of patient-specific signal metrics.

8. The device of claim 1, wherein the risk stratification circuit is configured to generate two or more categorical risk levels using a comparison between the composite risk index and a reference measure, the two or more categorical risk levels indicative of elevated risk of the patient later developing the event indicative of worsening of heart failure.

9. The device of claim 8, wherein the reference measure is computed using signal metrics of a patient population, at least a portion of the patient population having the first and the second demographic characteristic indicators.

10. A method of operating a medical device to determine a patient risk of worsening of heart failure, comprising:
receiving at least a first demographic characteristic indicator and a second demographic characteristic indicator of a patient via a patient status input unit included in a signal analyzer circuit, the second demographic characteristic indicator non-identical to the first demographic characteristic indicator;
receiving one or more physiologic signals of the patient via a signal receiver circuit;
generating a plurality of signal metrics from the one or more physiologic signals via a signal metrics generator circuit, including generating a first set of one or more signal metrics in response to the first demographic characteristic indicator meeting at least one first specified criterion, and generating a second set of signal metrics in response to the second demographic characteristic indicator meeting at least one second specified criterion;
selecting, via a patient-specific signal metric selector circuit, a subset of patient-specific signal metrics from the first and second sets of signal metrics based on signal metrics performance measures of at least one metric from the first and second sets of signal metrics;
generating, via a risk stratification circuit, a composite risk index using the selected subset of patient-specific signal metrics, the composite risk index indicative of the probability of the patient later developing an event indicative of worsening of heart failure; and
generating, via a risk report generator, a report to inform a user of an elevated risk of the patient developing the event indicative of worsening of heart failure.

11. The method of claim 10, wherein generating a composite risk index includes generating an indicator of probability of the patient developing a heart failure decompensation event within a specified timeframe.

12. The method of claim 10, further comprising receiving a first chronic disease indicator and a second chronic disease indicator of the patient, generating the first set of signal metrics further based on the first chronic disease indicator, and generating the second set of signal metrics further based on the second chronic disease indicator.

13. The method of claim 10, comprising
generating, for the first and second sets of signal metrics, respective signal metrics performance measures selected from the group consisting of a signal quality measure, a signal sensitivity measure, and a signal specificity measure; and
wherein selecting the subset of patient-specific signal metrics is based on the respective signal metric performance measures.

14. The method of claim 13, wherein generating the signal sensitivity measure includes calculating a relative change of the respective signal metric from a first state to a second state, the second state including temporal information non-identical to that of the first state.

15. The method of claim 10, wherein generating a composite risk index includes generating, for each metric in the selected subset of patient-specific signal metrics, respective risk scores using at least the first and the second demographic characteristic indicators, and calculating the composite risk index using the respective risk scores.

16. The method of claim 15, wherein calculating the composite risk index includes generating, for each metric in the selected subset of patient-specific signal metrics respective weight factors, and calculating the composite risk index using a combination of the respective risk scores respectively weighted by the weight factors.

17. The method of claim 16, wherein the weight factors for each metric in the selected subset of patient-specific signal metrics are determined using respective signal metrics performance measures.

18. The method of claim 10, further comprising categorizing the event indicative of worsening of heart failure into one of two or more categorical risk levels using a comparison between the composite risk index and a reference measure, the reference measure computed using signal metrics of a patient population having the first and the second demographic characteristics.

19. The system of claim 1, wherein the patient-specific signal metric selector circuit is configured to select the patient-specific signal metric subset including at least one signal metric from an intersection of the first and second sets of signal metrics.

20. The system of claim 1, wherein the patient-specific signal metric selector circuit is configured to select the patient-specific signal metric subset including at least one signal metric from the first set of signal metrics and at least one signal metric from the second set of signal metrics.

* * * * *